United States Patent [19]

Erdman et al.

[11] Patent Number: 4,716,037

[45] Date of Patent: Dec. 29, 1987

[54] METHOD OF ELIMINATING THE CORROSIVITY OF HAIR CONDITIONING COMPOSITIONS

[75] Inventors: Constance E. Erdman; Timothy J. Padden, both of Racine County, Wis.

[73] Assignee: S. C. Johnson & Son, Inc., Racine, Wis.

[21] Appl. No.: 832,565

[22] Filed: Feb. 24, 1986

[51] Int. Cl.$^4$ .......................... A61K 7/06; A61K 7/08
[52] U.S. Cl. ........................................ 424/70; 8/406; 424/74
[58] Field of Search ............................................ 424/70

[56] References Cited

FOREIGN PATENT DOCUMENTS

| 56-16405 | 2/1981 | Japan | 424/70 |
| 0077218 | 6/1981 | Japan | 424/70 |
| 0077614 | 5/1982 | Japan | 424/70 |
| 0077217 | 6/1984 | Japan | 424/70 |

Primary Examiner—Dale R. Ore

[57] ABSTRACT

The addition of a quaternary ammonium phosphate compound to hair conditioning compositions substantially prevents corrosion to stainless steel manufacturing equipment employed in the preparation of the hair conditioners.

18 Claims, No Drawings

METHOD OF ELIMINATING THE CORROSIVITY OF HAIR CONDITIONING COMPOSITIONS

BACKGROUND OF INVENTION

The present invention relates to a method of eliminating the corrosivity of hair conditioning compositions. In particular, the addition of a quaternary ammonium phosphate to hair conditioning compositions eliminates the corrosion of stainless steel which comes into contact with the hair conditioning composition during the manufacturing process.

Hair conditioning compositions, including creme rinses, are commonly applied to wet or dry hair to increase the combability, increase the body, and leave the hair with a natural feel. Hair conditioners should also leave hair shiny and manageable. Typical hair conditioning agents employed in hair conditioning compositions include quaternary ammonium compounds such as the quaternary ammonium sulfates and quaternary ammonium chlorides. Also employed as hair conditioning agents are amines neutralized with hydrochloric acid such as the stearyl dimethyl amine salt.

A problem associated with hair conditioning compositions is their corrosivity to stainless steel which comes in contact with the hair conditioning composition during the manufacturing process. Stainless steel equipment use for producing, pumping, homogenizing and transporting hair conditioning compositions during the manufacturing process can be damaged by hair conditioning compositions resulting in considerable economic loss to the equipment.

It has been unexpectedly found that the addition of quaternary ammonium phosphate compounds to hair conditioning compositions can eliminate the corrosion of the hair conditioning compositions to stainless steel. Additionally, it has been unexpectedly found that quaternary ammonium phosphates can be employed as the sole conditioning agent in hair conditioning compositions and exhibit no corrosion to stainless steel.

SUMMARY OF INVENTION

Briefly, in accordance with the present invention, an effective corrosion inhibiting amount of a quaternary ammonium phosphate compound is added to a hair conditioning composition to eliminate the corrosivity of the composition to stainless steel. The present hair conditioning compositions are noncorrosive to stainless steel machinery employed in the manufacture of the hair conditioning compositions.

The present quaternary ammonium phosphates are added to hair conditioning compositions during the manufacturing process to inhibit corrosion to the metal machinery and metal pipes in which the composition comes into contact with. The quaternary ammonium phosphates are added to the composition in amounts of from 0.1 percent by weight to about 5 percent by weight of the hair conditioning composition.

Of particular importance in the practice of the present invention, hydroxyethyl cetyldimonium phosphate is added to a hair conditioning intermediate composition to eliminate its corrosivity to stainless steel manufacturing equipment. The hydroxyethyl cetyldimonium phosphate is added to the hair conditioning intermediate compositions in amounts of from about 1 to about 10% by weight. Additionally, hair conditioning end product compositions employing hydroxyethyl cetyldimonium phosphate as the sole hair conditioning agent are noncorrosive to stainless steel.

DETAILED DESCRIPTION OF THE INVENTION

In practicing the present invention, a quaternary ammonium phosphate compound is added to a corrosive hair conditioning composition. The quaternary ammonium phosphate compound substantially prevents corrosion of stainless steel hardware which comes into contact with the hair conditioning composition during the manufacturing process. The quaternary ammonium phosphate compounds do not adversely affect the properties of the hair conditioning compositions.

Suitable quaternary ammonium phosphate compounds include those compounds of the formula:

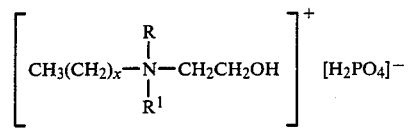

where x represents 8 to 22, inclusive, and R and $R^1$ each independently represent an alkyl group having up to 22 carbon atoms. Preferably R and $R^1$ represent a lower alkyl ($C_1$–$C_4$) such a methyl. Mixtures of these compounds can also be employed.

The quaternary ammonium phosphate compounds are added to the present hair conditioning compositions in amounts which prevent corrosion of stainless steel hardware which comes into contact with the hair conditioning compositions during the manufacturing process. Generally the quaternary ammonium phosphate compounds are added to the hair conditioning compositions in amounts of from about 0.1 to about 4% by total weight of the end-use hair conditioning composition, advantageously from about 0.5 to about 3% by weight of the total hair conditioning composition and preferably from about 0.75 to about 1.25% by total weight of the hair conditioning composition. The above percentages are based on the total weight of an end-product hair conditioning composition, i.e., a ready-to-use hair conditioner. The concentration of quaternary ammonium phosphate in an intermediate hair conditioning composition usually ranges from about 1 to about 10 percent by weight but upon dilution with water and other cosmetic additives would fall into the range for end-product concentrations, i.e., 0.1–4.0%.

The quaternary ammonium phosphate compounds can be added to the hair conditioning compositions in addition to the other commonly used hair conditioning agents or, alternatively, the quaternary ammonium phosphate compounds may be added to the present hair conditioning compositions as a substitute for the standard hair conditioning agents, i.e., the quaternary ammonium phosphate compound serves the dual function of a corrosion inhibitor and a hair conditioning agent. When the present quaternary ammonium phosphate compounds are employed in combination with other quaternary hair conditioning agents, i.e., chloride (Cl) or sulfate ($SO_4$) ion-forming compounds, the weight ratio of quaternary ammonium phosphate compound/Cl or $SO_4$ hair conditioning agent is from about 1:1 to about 2:1. When the present quaternary ammonium phosphate compounds are employed as the sole conditioning agent then they are preferably present in amounts of from about 2 to about 4% by weight of the hair conditioning composition.

The other components of the present hair conditioning compositions are standard hair conditioning ingredients and include standard hair conditioning agents, polymeric setting agents, waxy materials (higher alcohols), protective colloids, perfumes, preservatives, dyes, herbs, biocides, thickening agents, and the like.

The bulk of the present hair conditioning compositions comprises water, i.e., in the range of from about 80–99% by weight. Although tap water can sometimes be used if the same contains a relatively low level of ions, it is preferred to use deionized water.

All of the above-described hair conditioning ingredients are well known to one skilled in the art and are employed in concentrations readily determinable by one skilled in the art. Conventional creme rinse formulations and methods of preparing them are disclosed in the Chemistry and Manufacture of Cosmetics, Volume 4, Second Edition, by Maison G. DeNavarre; U.S. Pat. No. 4,421,740; and Harry's Cosmeticology, 6th Edition, all of which are incorporated herein by reference.

In formulating the present hair conditioning compositions, the quaternary ammonium phosphate compounds, water and any other additional hair conditioning and/or cosmetic additives are admixed employing standard procedures well known to one skilled in the art. Optionally, the ingredients may be admixed at an elevated temperature and homogenized employing standard techniques. See the Chemistry and Manufacture of Cosmetics, Volume 4, Second Edition and U.S. Pat. No. 4,421,740. The quaternary ammonium phosphate compounds are preferably added to the hair conditioning composition during the manufacturing process before, or when, the ingredients which are responsible for corrosion are added.

The hair conditioning compositions of the present invention can be the finished creme rinse or hair conditioner products or an intermediate employed in the manufacture of creme rinses and hair conditioners. Sometimes the final product will not be corrosive to some metals because the concentration of corrosive ingredients is insufficient to cause corrosion. Additionally, it is known that perfumes sometime inhibit corrosion. During the manufacturing process it is common to employ a hair conditioning intermediate which has high concentrations of the chloride of methosulfate ion containing hair conditioners. Such hair conditioning intermediate compositions, and especially those not containing perfumes, present a serious problem with regard to the corrosion of metal manufacturing equipment and in particular stainless steel. It is an important aspect of the present invention to prevent such intermediate compositions from causing corrosion to metal manufacturing equipment.

Hair conditioning intermediate compositions will contain a chloride and/or sulfate ion containing hair conditioning agent, i.e., quaternary ammonium chloride or methosulfate and/or a conditioning amine that has been neutralized with hydrochloric acid, quaternary ammonium phosphate compound and water. Optional ingredients include polymeric setting agents, fatty alcohols and mineral oil. After the hair conditioning intermediate is prepared, it is admixed with a thickener intermediate to produce the final creme rinse composition.

The thickener intermediate is an aqueous mixture containing water and a thickening agent, i.e., hydroxyethyl cellulose at a 0.5–1.5 weight percent based on the total weight of the final ready-to-use hair conditioner, and, optionally, standard cosmetic additives described herein before such as protein, humectants, preservatives, biocides, dyes, herbs, perfumes and the like. The exact ratio of hair conditioning intermediate and thickener intermediate employed in preparing the finished hair conditioning composition product will depend upon the concentrations of ingredients in each. The intermediates will be admixed in amounts sufficient to form a finished hair conditioner or creme rinse having acceptable levels of all the ingredients.

Typical hair conditioning intermediate compositions according to the present invention include the following:

| INTERMEDIATE FORMULATION A | | |
|---|---|---|
| | Weight % | |
| Ingredients | Preferred | Range |
| Quaternary ammonium phosphate* | 1.5 | 1–4 |
| Stearyalkonium chloride | 1.2 | 1–3 |
| Amine HCL | 0.2 | 0–1 |
| Mineral oil | 4.0 | 0–6 |
| Fatty alcohol | 5.0 | 1–10 |
| Water | qs 100.0 | qs 100.0 |

*at least equal in weight to stearyalkonium chloride

| INTERMEDIATE FORMULATION B | | |
|---|---|---|
| | Weight % | |
| Ingredients | Preferred | Range |
| Quaternary ammonium phosphate | 3.0 | 1–10 |
| Fatty alcohol | 4.8 | 0–10 |
| Mineral Oil | 4.0 | 0–6 |
| Water | qs 100.0 | qs 100.0 |

In a preferred embodiment of the present invention, hydroxyethyl cetyldimonium phosphate is employed as the quaternary ammonium phosphate compound. Hydroxyethyl cetyldimonium phosphate is commercially available as BINA QAT 44C from Dyestuffs and Chemical Division of Ciba-Geigy, P.O. Box 18300, Greensboro, N.C. 27419. Typical hydroxyethyl cetyldimonium phosphate formulations according to the present invention include the following:

| INTERMEDIATE FORMULATION C | | |
|---|---|---|
| | Weight % | |
| Ingredients | Preferred | Range |
| Hydroxyethyl cetyldimonium phosphate* | 1.5 | 1–4 |
| Stearyalkonium chloride | 1.2 | 1–3 |
| Amine HCL | 0.2 | 0–1 |
| Mineral oil | 4.0 | 0–6 |
| Fatty alcohol | 5.0 | 0–10 |
| Water | qs 100.0 | qs 100.0 |

*at least equal in weight to stearyalkonium chloride

| INTERMEDIATE FORMULATION D | | |
|---|---|---|
| | Weight % | |
| Ingredients | Preferred | Range |
| Hydroxyethyl cetyldimonium phosphate | 3.0 | 1–10 |
| Fatty alcohol | 4.8 | 0–10 |
| Mineral oil | 4.0 | 0–6 |
| Water | qs 100.0 | qs 100.0 |

In preparing a creme rinse hair conditioning intermediate composition the water, fatty alcohol, quaternary ammonium phosphate and other hair conditioning agents are charged to an appropriate vessel and heated with agitation to a temperature of between about 120° F. and about 150° F. The mineral oil is then added to the vessel and the mixture heated with agitation to a temperature of between about 160° F. and 180° F. The mixture is then cooled to room temperature. The quaternary ammonium phosphate compound is charged to the vessel before, or at, the time that the corrosive conditioning agent(s) is charged to the vessel. The quaternary ammonium phosphate is added to the intermediate mixture in amounts of about 1 to about 10 percent by weight. When BINA QAT 44C is employed as the quaternary ammonium phosphate, it must be taken into account that BINA QAT 44C is approximately 30% active ingredient. The addition of the quaternary ammonium phosphate will prevent corrosion to stainless steel manufacturing equpiment which comes into contact with the intermediate composition. This intermediate composition can then be stored for future use or can be immediately admixed with a thickening intermediate to prepare a finished creme rinse product.

The hair conditioning compositions according to the present invention are noncorrosive to stainless steel which comes into contact with the hair conditioning formulation during the manufacturing process. The passive nature of the present compositions can be determined employing standard potentiodynamic scanning tests on the compositions.

The hair conditioning compositions of the present invention are (1) intermediate compositions used in formulating end-use hair conditioners or (2) ready-to-use hair conditioners or creme rinses which are applied directly to the hair of the user subsequent to shampooing. These compositions are easily and readily dispersible across the hair fibers and forms substantially thin films on the hair fibers to replace the oils which are stripped from the hair during shampooing. Also, the present compositions can be readily dispersed in small quantities of water.

The following examples illustrate the practice of the present invention but should not limit its scope. All percentages are by weight, unless specified otherwise.

EXAMPLE 1: HAIR CONDITIONING INTERMEDIATE

The following ingredients were formulated into a hair conditioning intermediate composition which is noncorrosive to stainless steel:

| Ingredients | Weight %* |
|---|---|
| Bina Qat 44C brand hydroxyethyl cetyldimonium phosphate | 1.5 |
| Stearylalkonium chloride | 1.2 |
| Amine HCL | 0.2 |
| Mineral oil | 4.0 |
| Fatty alcohol | 5.0 |
| Water | qs 100.0 |

*weight percent active ingredient

A potentiodynamic scanning was conducted on the above formulation and that formulation was found to be passive on 316 stainless steel. This intermediate composition was then admixed with a thickener composition in a weight ratio of three (3) parts thickener to one (1) part intermediate resulting in a ready-to-use hair conditioner.

EXAMPLE 2: HAIR CONDITIONING INTERMEDIATE EMPLOYING A QUATERNARY AMMONIUM PHOSPHATE AS THE SOLE CONDITIONING AGENT

The following ingredients were formulated into a hair conditioning intermediate composition which is noncorrosive to stainless steel:

| Ingredients | Weight %* |
|---|---|
| Bina Qat 44C brand hydroxyethyl cetyldimonium phosphate | 3.0 |
| Fatty alcohol | 4.8 |
| Mineral oil | 4.0 |
| Water | qs 100.0 |

*weight percent active ingredient

A potentiodynamic scanning test was conducted on the above formulation and that formulation was found to be passive on 316 stainless steel. This intermediate composition was then admixed with a thickener composition in a weight ratio of three (3) parts thickener to one (1) part intermediate resulting in a ready-to-use hair conditioner.

In other representative operations of the present invention, various quaternary ammonium phosphates, described herein, are added to hair conditioning intermediate and ready-to-use compositions to eliminate the corrosion of stainless steel.

We claim:

1. A method of eliminating the corrosion to stainless steel by a corrosive hair conditioning composition which contains chloride ions or sulfate ions and is corrosive to stainless steel which comprises adding to the corrosive hair conditioning composition an effective corrosion inhibiting amount of a quaternary ammonium phosphate compound.

2. The method of claim 1 wherein the quaternary ammonium phosphate compound is a compound of the formula:

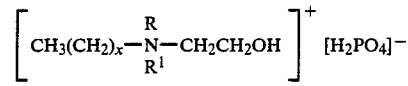

wherein x represents 1–22, inclusive, and R and R¹ each independently represent an alkyl group having up to 22 carbon atoms.

3. The method of claim 2 wherein R and R¹ each independently represent methyl.

4. The method of claim 3 wherein the quaternary ammonium phosphate compound is hydroxyethyl cetyldimonium phosphate.

5. The method of claim 4 wherein hair conditioning composition is a ready-to-use hair conditioner and the hydroxyethyl cetyldimonium phosphate is present in said composition in an amount of from about 0.1 to about 4% by weight.

6. The method of claim 5 wherein the hydroxyethyl cetyldimonium phosphate is present in an amount of from about 0.5 to about 3% by weight.

7. The method of claim 5 wherein the hydroxyethyl cetyldimonium phosphate is added to the hair conditioning composition in addition to other hair conditioning agents containing chloride ions or sulfate ions.

8. The method of claim 5 wherein the hydroxyethyl cetyldimonium phosphate is added to the hair conditioning composition as the sole hair conditioning agent.

9. The method of claim 4 wherein the hair conditioning composition is an intermediate composition and the hydroxyethyl cetyldimonium phosphate is present in said composition in an amount of from about 1–10% by weight.

10. The method of claim 9 wherein the hydroxyethyl cetyldimonium phosphate is present in said intermediate composition in an amount of from about 2 to about 6% by weight.

11. The method of claim 9 wherein the hydroxyethyl cetyldimonium phosphate compound is added to the intermediate composition in an amount which is at least about equal in weight to other hair conditioning agents present in said composition.

12. The method of claim 9 wherein the hydroxyethyl cetyldimonium phosphate is added to the intermediate composition as the sole hair conditioning agent.

13. In a hair conditioning intermediate composition which comes in contact with stainless steel manufacturing equipment prior to packaging the finished compositions, which contains a chloride ion or sulfate ion containing hair conditioning agent and is corrosive to stainless steel, the improvement which comprises adding to said hair conditioning composition an effective corrosion inhibiting amount of a quaternary ammonuim phosphate compound before said conditioning agent can act to corrode the stainless steel whereby the resulting hair conditioning intermediate composition is substantially noncorrosive to stainless steel.

14. The improved hair conditioning intermediate composition of claim 13 wherein the quaternary ammonium phosphate compound is a compound of the formula:

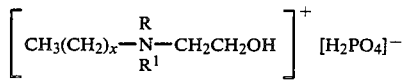

wherein x represent 1–22, inclusive, and R and $R^1$ each independently represent an alkyl group having up to 22 carbon atoms.

15. The improved hair conditioning intermediate composition of claim 14 wherein R and $R^1$ each independently represent methyl.

16. The improved hair conditioning intermediate composition of claim 15 wherein the quaternary ammonium phosphate compound is hydroxyethyl cetyldimonium phosphate.

17. The improved hair conditioning intermediate composition of claim 16 wherein the hydroxyethyl cetyldimonium phosphate is present in said composition in an amount which is at least about equal in weight to other conditioning agents containing chloride ions or sulfate ions present in said intermediate composition.

18. The improved hair conditioning intermediate composition of claim 17 wherein the hydroxyethyl cetyldimonium phosphate is present in an amount of from about 0.5 to about 3% by weight.

* * * * *